(12) United States Patent
Kapila et al.

(10) Patent No.: US 7,015,365 B2
(45) Date of Patent: Mar. 21, 2006

(54) METHODS FOR PREPARING CYCLOALKYLIDENE BISPHENOLS

(75) Inventors: Debjani Kapila, Bangalore (IN); Ramesh Krishnamurti, Bangalore (IN); Jan-Pleun Lens, Breda (NL); Gurram Kishan, Bangalore (IN); Nileshkumar Kukalyekar, Sangli (IN); Jegadeesh Thampi, Bangalore (IN); Umesh Krishna Hasyagar, Bangalore (IN); Vinod Kumar Rai, Bangalore (IN); Ashok S. Shyadligeri, Bangalore (IN); Radhakrishna Sreenivasarao Arakali, Bangalore (IN); Edward J. Nesakumar, Bangalore (IN); Pramod Kumbhar, Bangalore (IN)

(73) Assignee: General Electric Company, Schenectady, NY (US)

( * ) Notice: Subject to any disclaimer, the term of this patent is extended or adjusted under 35 U.S.C. 154(b) by 29 days.

(21) Appl. No.: 10/742,474

(22) Filed: Dec. 19, 2003

(65) Prior Publication Data

US 2005/0137428 A1 Jun. 23, 2005

(51) Int. Cl.
*C07C 39/17* (2006.01)
(52) U.S. Cl. .................................... 568/721
(58) Field of Classification Search ............... 568/721
See application file for complete search history.

(56) References Cited

U.S. PATENT DOCUMENTS

| | | | | |
|---|---|---|---|---|
| 3,242,219 | A | * 3/1966 | Farnham et al. | 568/728 |
| 4,052,466 | A | * 10/1977 | Sun | 568/728 |
| 4,191,843 | A | 3/1980 | Kwantes et al. | |
| 4,319,053 | A | * 3/1982 | Heuser et al. | 568/727 |
| 4,387,251 | A | 6/1983 | Meyer et al. | 568/727 |
| 4,554,309 | A | * 11/1985 | Mark et al. | 524/611 |
| 4,766,255 | A | 8/1988 | Ong et al. | 568/728 |
| 4,859,803 | A | 8/1989 | Shaw | |
| 4,982,014 | A | * 1/1991 | Freitag et al. | 568/721 |
| 5,210,328 | A | * 5/1993 | Freitag et al. | 568/721 |
| 5,276,213 | A | * 1/1994 | Serini et al. | 568/721 |
| 6,284,931 | B1 | * 9/2001 | Isota et al. | 568/721 |
| 6,486,222 | B1 | 11/2002 | Kissinger et al. | |
| 6,646,097 | B1 | 11/2003 | Shyadligeri et al. | 528/196 |

FOREIGN PATENT DOCUMENTS

| | | | |
|---|---|---|---|
| DE | 1242237 A | * | 6/1967 |
| DE | 4032595 A | * | 4/1992 |
| EP | 0481287 A2 | | 4/1992 |
| EP | 0 342 758 B1 | | 5/1995 |
| GB | 1 539 184 | | 1/1979 |
| WO | 02/50000 A1 | | 6/2002 |

OTHER PUBLICATIONS

"Product Data Sheet Aberlyst 16WET"; Nov. 2003; ROHM AND HAAS; http://www.rohmhaas.com/lonexchange/IP/literaturea4/16wet.pdf>; 2 pages.
Eastmond G.C. et al.; "Synthesis of Bulky Bis(ether Anhydride)s and Poly(ether Imide)s with Bulky Main-Chain Units"; Journal of Material s Chemistry, Cambridge, GB, vol. 7, No. 4, Apr. 1997; pp. 589-592.
International Search Report; International Application No. PCT/US2004/038270; International Filing Date: Nov. 16, 2004; Date of Mailing: Jun. 13, 2005; 9 pages.

* cited by examiner

*Primary Examiner*—Michael L. Shippen

(57) ABSTRACT

A process for forming a cycloalkylidene bisphenol comprises: reacting a cycloalkanone compound of formula:

$$\underset{R^4}{\overset{R^4}{\underset{R^4}{\overset{R^4}{\bigvee}}}} \overset{O}{\underset{(CR^1R^2)_a}{\bigvee}} (CR^3R^4)_b;$$

where [A] is a substituted or an unsubstituted aromatic group, $R^1$–$R^4$ independently represent a hydrogen or a $C_1$–$C_{12}$ hydrocarbyl group; and "a" and "b" are integers independently having values from 0–3; with an aromatic hydroxy compound of formula [A]-OH, where [A] is as previously described; at a mole ratio of greater than or equal to about 20, in the presence of a sulfonic acid type ion exchange resin catalyst crosslinked with greater than or equal to about 8 weight percent of divinylbenzene, and a promoter selected from the group consisting of a mercaptan compound and a resorcinol compound; to form a cycloalkylidene bisphenol of formula:

$$\underset{HO}{\overset{[A]}{\underset{[A]}{\bigvee}}} \overset{R^4}{\underset{(CR^1R^2)_a}{\bigvee}} (CR^3R^4)_b;$$

where [A], $R^1$–$R^4$, "a" and "b" are as previously described. Moreover, any acid catalyst can be used with a resorcinol promoter.

21 Claims, No Drawings

METHODS FOR PREPARING CYCLOALKYLIDENE BISPHENOLS

BACKGROUND

The present disclosure relates generally to methods for producing cycloalkylidene bisphenols. More particularly, the disclosure relates to methods for producing cycloalkylidene bisphenols using macroreticular sulfonic acid type ion exchange resins as catalysts, and mercaptan and/or a resorcinol compounds as promoters.

Cycloalkylidene bisphenols are valuable raw materials for producing polycarbonates having enhanced properties, such as thermal stability, clarity, and dimensional stability in the presence of moisture. The para, para-isomers are particularly valuable in this regard. Cycloalkylidene bisphenols have generally been prepared by a condensation reaction of an aromatic hydroxy compound with a cycloalkanone using an acid catalyst to catalyze this reaction. In addition to the acid catalyst, a promoter is also used to further aid the reaction. Mineral acids, such as hydrochloric acid or sulfuric acid have been generally used for producing cycloalkylidene bisphenols as promoters.

Sulfonic acid type ion exchange resin catalysts, particularly the so-called gelular ion exchange resin catalysts, which are crosslinked with up to 4 weight percent of divinylbenzene have been widely used as catalysts for preparing aromatic dihydroxy compounds. For example, gelular ion exchange resins have been used in conjunction with mercaptan compounds to produce para, para-bisphenol A, which is one of the more important aromatic dihydroxy compounds used for producing polycarbonate homopolymers and copolymers. Although the gelular resins perform satisfactorily for bisphenol A, they exhibit low selectivity and reactivity for producing cycloalkylidene bisphenols, and in particular, the para, para-isomer. Prior art gelular resins crosslinked at less than or equal to about 4 weight percent of DVB are used in a continuous process for producing bisphenols, particularly bisphenol A, compression of the catalyst particles due to hydrostatic pressure occurs, and this hydraulically limits the process.

Accordingly, there remains a need in the art for more efficient methods to prepare cycloalkylidene bisphenols, which exhibit improved selectivity and reactivity than gelular resins.

BRIEF SUMMARY

In one embodiment of the disclosure, a process for producing a cycloalkylidene bisphenol comprises: reacting a mixture comprising an aromatic hydroxy compound and a cycloalkanone in the presence of a sulfonic acid type ion exchange resin catalyst and a promoter; where the aromatic hydroxy compound and the cycloalkanone are present in a mole ratio greater than or equal to about 20; the sulfonic acid type ion exchange resin catalyst is crosslinked with greater than about 8 weight percent of divinylbenzene relative to the overall weight of the sulfonic acid type ion exchange resin catalyst; the promoter is selected from the group consisting of a mercaptan compound and a resorcinol compound; the cycloalkylidene bisphenol has the formula:

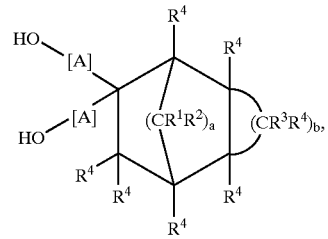

where [A] is a substituted or an unsubstituted aromatic group, $R^1$–$R^4$ independently represents a hydrogen or a $C_1$–$C_{12}$ hydrocarbyl group; and "a" and "b" are integers independently having values from 0–3.

In a second embodiment of the disclosure, a method for preparing a cycloalkylidene bisphenol comprises: reacting a mixture comprising an aromatic hydroxy compound and a cycloalkanone in the presence of an acid catalyst and a promoter, where the promoter comprises a resorcinol compound, and the cycloalkylidene bisphenol has the formula:

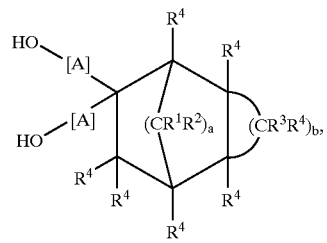

where [A] is a substituted or an unsubstituted aromatic group, $R^1$–$R^4$ independently represents a hydrogen or a $C_1$–$C_{12}$ hydrocarbyl group; and "a" and "b" are integers independently having values from 0–3.

In a third embodiment of the disclosure, a method for producing 1,1-bis(3-methyl-4-hydroxyphenyl)cyclohexane comprises: reacting a mixture comprising ortho-cresol and cyclohexanone in the presence of from 10 to 15 weight percent of dodecylbenzenesulfonic acid, relative to a combined weight of ortho-cresol and cyclohexanone; and from 5000 to 15000 parts of resorcinol per million parts of the combined weights of cyclohexanone and ortho-cresol to form 1,1-bis(3-methyl-4-hydroxyphenyl)cyclohexane.

In a fourth embodiment of the disclosure, a method for producing a substituted or an unsubstituted bis(hydroxyaryl)tricyclo[5.2.1.0$^{2.6}$]decane, said method comprises: reacting a substituted or an unsubstituted tricyclo[5.2.1.0$^{2.6}$]decanone with an aromatic hydroxy compound in the presence of a sulfonic acid type ion exchange resin catalyst and a promoter; wherein said ion exchange resin catalyst is crosslinked with greater than or equal to about 8 weight percent of divinylbenzene relative to the overall weight of said sulfonic acid type ion exchange resin catalyst; and forming said substituted or unsubstituted bis(hydroxyaryl)tricyclo[5.2.1.0$^{2.6}$]decane.

These and other embodiments are more clearly explained with illustrative examples in the following detailed description.

DETAILED DESCRIPTION

The many embodiments described in this disclosure have the advantage of providing versatile methods for producing cycloalkylidene bisphenols of the formula (I):

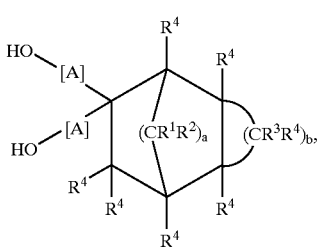

(I)

where [A] is a substituted or an unsubstituted aromatic group, $R^1$–$R^4$ independently represent a hydrogen or a $C_1$–$C_{12}$ hydrocarbyl group; and "a" and "b" are integers independently having values from 0–3. These cycloalkylidene bisphenols can be conveniently prepared in high yield and selectivity by reacting cycloalkanones of formula (II):

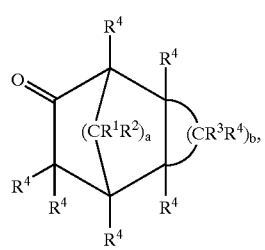

(II)

with aromatic hydroxy compounds of formula [A]-OH in the presence of a sulfonic acid type ion exchange resin catalyst and a promoter selected from the group consisting of a mercaptan compound and a resorcinol compound; where $R^1$–$R^4$, [A], "a", and "b" are as described previously for formula (I). Throughout this disclosure, the term "sulfonic acid type ion exchange resin catalyst" is also sometimes referred to as "catalyst".

Preferred sulfonic acid ion exchange resin catalysts are polystyrene resins that are crosslinked with greater than about 8 weight percent of divinylbenzene relative to the overall weight of the sulfonic acid type ion exchange resin catalyst. Divinylbenzene (hereinafter sometimes referred to as "DVB") is generally used as a crosslinking agent during the preparation of the cross-linked polystyrene, prior to the sulfonation step, which produces the sulfonic acid type polystyrene-based ion exchange resin.

In another embodiment, preferred sulfonic acid ion exchange resins suitable for preparing the bisphenols of formula (I) are polystyrene resins that are crosslinked with greater than or equal to about 8 weight percent of divinylbenzene relative to the overall weight of the sulfonic acid type ion exchange resin catalyst. More preferably, the sulfonic acid type ion exchange resins are those that are crosslinked with greater than or equal to about 18 weight percent of divinylbenzene. Sulfonic acid type ion exchange resin catalysts crosslinked with about 20 weight percent divinylbenzene are particularly preferred since these show very high catalytic activity, and are widely available commercially. Examples of suitable sulfonic acid type ion exchange resins include, but are not limited to Amberlyst® 15 (a polystyrene resin crosslinked with about 20 weight percent of divinylbenzene, available commercially from Rohm and Haas Company), T-66 (a polystyrene resin crosslinked with about 8 weight percent of divinylbenzene) and T-63 (a polystyrene resin crosslinked with about 18 weight percent of divinylbenzene). T-63 and T-66 ion exchange resins are available commercially from Thermax Limited.

Sulfonic acid type ion exchange resin catalysts having greater than or equal to about 8 weight percent divinylbenzene crosslinking are also useful in a continuous process for preparing the bisphenols of formula (I). However, it is also noted that a batch process or a semi-continuous process can also be employed with advantageous results. The catalyst is used in combination with a promoter selected from the group consisting of a resorcinol compound, a mercaptan compound, and mixture thereof. In one embodiment, such catalysts are valuable for preparing 5,5-bis(4-hydroxyphenyl)tricyclo[$5.2.1.0^{2,6}$]decane (hereinafter also referred to as "TCDBP"). Other examples of cycloalkylidene bisphenols that can be prepared using these catalysts include, but are not limited to, 1,1-bis(3-methyl-4-hydroxyphenyl)cyclohexane (hereinafter referred to as "DMBPC"), 1,1-bis(3-methyl-4-hydroxyphenyl)perhydrocumylcyclohexane, and the like. In other embodiments, cycloalkylidene bisphenols based on condensation products of a substituted or an unsubstituted phenol with 3,3,5-trimethylcyclohexanone can also be prepared with the sulfonic acid type ion exchange resin catalyst and promoter.

In the continuous process, a mixture comprising an aromatic hydroxy compound, a cycloalkanone of formula (II), and a promoter are passed through a reactor packed with a sulfonic acid type ion exchange resin catalyst crosslinked with greater than about 8 weight percent of divinylbenzene relative to the overall weight of the ion exchange resin catalyst. A weight hourly space velocity (abbreviated as "WHSV") of about 0.25 to about 4 is used, and more preferably, the WHSV is about 0.5 to about 1.5. These reactions are conducted by employing a mole ratio of the aromatic hydroxy compound to the cycloalkanone that is greater than or equal to about 20. Mole ratios greater than 18, such as for example from about 25 to about 30, are preferred since lifetime of the catalyst is extended while maintaining catalytic activity and selectivity for the p,p-cycloalkylidene bisphenol. By the term, "maintaining catalytic activity" is meant that the catalytic activity is greater than or equal to about 70 percent of an initial catalytic activity, which is measured after about 16 hours of run time in one embodiment, and after about 24 hours of run time in another embodiment. In a continuous process the amount of cycloalkylidene bisphenol measured in the effluent increases steadily over time and generally tends to level off. Typically, the catalytic activity tends to fluctuate at the initial stages of the process, but after about 16 to 24 hours, the fluctuation in the catalytic activity tends to level off. Without wishing to be bound by any theory, it is believed that a higher mole ratio of the aromatic hydroxy compound to the cycloalkanone prevents fouling of the pores present in the ion exchange resin catalyst particles, thereby maintaining catalyst activity and product selectivity. Another advantage of such highly crosslinked ion exchange resin catalysts (often called "macropore ion exchange resins") is that when they are used in a packed bed continuous process, they tend to hold up to hydrostatic pressure buildup over a long period of time (running to several hundred hours, as will be evident from the discussion further below) without any significant loss in catalytic activity and product selectivity. The higher crosslink density helps in increasing the rigidity of the catalyst particles. When prior art gelular resin catalysts cross-linked with about 2 weight percent of DVB are used in a continuous process for producing bisphenols, particularly bisphenol A, compression of the catalyst bed due to hydrostatic pressure occurs, and this hydraulically limits the process. Hydraulic limitations can be overcome by using a combination catalyst bed comprising 2 weight percent and 4 weight percent DVB crosslinked ion exchange resin catalysts, such as for example, disclosed in U.S. Pat. No. 6,486,222. Applicants have found that the sulfonic acid type ion exchange resin catalysts having greater than or equal to about 8 weight percent divinylbenzene crosslinking are more selective and active catalysts for producing cycloalkylidene bisphenols, such as DMBPC and TCDBP, when used in combination with a promoter selected from the group consisting of a mercaptan compound, a resorcinol compound, and mixtures thereof. Furthermore, these catalysts have high catalyst activity even after long run times of greater than or equal to about 600 hours, when tested in packed bed reactors in a continuous mode. Due to the higher crosslinking, these resin particles are capable of overcoming hydraulic limitations, that is they are capable of maintaining efficient pressure drop levels; and are less prone to breakage. Therefore, the catalyst bed requires less frequent changeovers, thus minimizing lost production time.

The cycloalkylidene bisphenols produced by the techniques described in this disclosure predominantly comprise the p,p'-isomer. When hindered cycloalkanones and/or hindered aromatic hydroxy compounds are used, the p,p'-bisphenol isomer is practically the only product formed. Isolation of purified p,p'-cycloalkylidene bisphenol can be generally accomplished by techniques, such as crystallization or fractional crystallization from a suitable solvent, or distillation.

The continuous process described above may be carried at any temperature from about 40° C. to about 120° C., more preferably from about 50° C. to about 100° C. In general, the lower temperature limit may correspond to the lowest temperature at which a given aromatic hydroxy compound will remain as a liquid. A solvent can be used for the process, but it will generally lead to additional process steps and higher process cost. Moreover, the continuous reactions as described above enables the preparation of cycloalkylidene bisphenols with high catalytic activity of greater than or equal to about 70 percent relative to the initial catalytic activity, which has been previously described.

As previously discussed, the promoter is selected from the group consisting of a mercaptan compound, a resorcinol compound, and mixtures thereof. Non-limiting examples of suitable mercaptan compounds include 3-mercaptopropionic acid (hereinafter called 3-MPA), a substituted or an unsubstituted benzyl mercaptan, 3-mercapto-1-propanol, ethyl 3-mercaptopropionate, 1,4-bis(mercaptomethyl)benzene, alkanethiols of the formula R-SH, wherein "R" is a $C_1$ to $C_{10}$ aliphatic group; and mixtures of the foregoing mercaptan promoters. 3-mercaptopropionic acid is a preferred promoter since it is a commercially readily available, inexpensive material.

Alternatively, the mercaptan compound has a nitrogen-containing group, where the nitrogen is capable of getting protonated by the sulfonic acid type ion exchange resin. The nitrogen-containing group is preferably an acyclic or heterocyclic nitrogen-containing group, such as, for example, aminoethyl, pyridylalkyl, and the like. Some specific examples of mercaptan compounds having a nitrogen-containing group include 2-aminoethyl mercaptan, (4mercaptoethyl)pyridine, (2-mercaptoethyl)pyridine, and (3-mercaptoethyl)pyridine. When such promoters are used with a sulfonic acid type ion exchange resin catalyst, an ionic bond is formed between the nitrogen atom and the sulfonic acid group. This ionic bond leads to an immobilization of the mercaptan promoter on the ion exchange resin catalyst.

Other suitable mercaptan promoters include mercaptan precursors, which transforms into a mercaptan compound having an SH group in the presence of the sulfonic acid type ion exchange resin catalyst and an aromatic hydroxy compound. In one embodiment, the mercaptan precursor generally comprises an alkylthio derivative of a mercaptan compound, or a substituted or an unsubstituted 1,3-thiazolidine. Other types of mercaptan precursors include acylthio derivatives of mercaptans. Adventitious water present in the reaction mixture may generally aid in conversion of the mercaptan precursor into the corresponding mercaptan compound. Water present either in the raw materials or generated from the reaction may be adequate to convert the mercaptan precursor into an effective amount of the mercaptan compound.

Suitable resorcinol compounds are generally of the formula (III):

where $R^5$ is selected from the group consisting of hydrogen, chlorine, fluorine, bromine, and $C_1$–$C_{10}$ alkyl groups; and $R^6$ and $R^7$ are independently selected from the group consisting of $C_1$–$C_{10}$ alkyl groups. In an embodiment, the resorcinol compound is selected from the group consisting of resorcinol, 2-methylresorcinol, resorcinol diethyl ether, resorcinol dimethylether, 4-hexylresorcinol, 4-chlororesorcinol, and any combinations of the foregoing resorcinol compounds. More preferably, the resorcinol compound is resorcinol since it is an inexpensive, commercially available material.

In one embodiment, the cycloalkylidene bisphenol can also be produced using a promoter mixture comprising one or more resorcinol compounds of formula (III) and one or more mercaptan compounds described previously. This aspect can be advantageous, such as for example, when it is required to change the promoter from a mercaptan compound to a resorcinol compound in a production train without having to shut down the process or adversely affect the purity of the final product. This is further evident from the Examples discussed further below, where resorcinol promoters exemplified by resorcinol exhibit selectivity for para,para-DMBPC When a resorcinol compound is used as a promoter, any type of acid catalyst can be used for producing a cycloalkylidene bisphenol. The acid catalyst comprises a hydrogen halide of the formula HX, wherein "X" is selected from the group consisting of fluoride, chloride, bromide, and iodide; sulfuric acid, an organic sulfonic acid, or a sulfonic acid type ion exchange resin catalyst having a crosslink density of divinylbenzene greater than or equal to about 8 weight percent. A preferred organic sulfonic acid is selected from the group consisting of methanesulfonic acid, naphthalenesulfonic acid, p-toluenesulfonic acid, and dodecylbenzenesulfonic acid. DVB-crosslinked polystyrene resins having greater than or equal to about 8 weight percent of DVB relative to the overall weight of the resin are preferred catalysts since these catalysts are less corrosive than mineral acid catalysts, such as hydrogen chloride; and therefore do not require the use of the more expensive glass-lined equipment. Cycloalkylidene bisphenols can be prepared by using a mole ratio of an aromatic hydroxy compound to a cycloalkanone of greater than about 2 in one embodiment, more preferably greater than or equal to about 20 in another embodiment.

In another embodiment, any combination of one or more mercaptan compounds, mercaptan precursors, and resorcinol compounds can be used as a promoter in combination with the sulfonic acid type ion exchange resin catalyst for producing a cycloalkylidene bisphenol.

A wide variety of aromatic hydroxy compounds can be used for the methods disclosed in this disclosure. Non-limiting examples of aromatic hydroxy compounds include phenol, ortho-cresol, meta-cresol, para-cresol, 2,6-xylenol, and mixtures of the foregoing aromatic hydroxy compounds.

In carrying out the preparation of a cycloalkylidene bisphenol, the corresponding aromatic hydroxy compound and cycloalkanone are preferably at a mole ratio greater than or equal to about 20. The preferred mole ratio to be used depends upon, among other factors, the solubility of the cycloalkylidene bisphenol in the reaction mixture; the nature of the process, such as a batch, continuous, or semi-continuous process; and the reaction temperature. For example, for preparing TCDBP continuously using Amberlyst® 15 catalyst and a promoter (resorcinol or mercaptan compound) at a reaction temperature of about 100° C., a mole ratio of phenol to tricyclo[5.2.1.0$^{2,6}$]decanone (TCD) at about 18 to about 100 is used in one embodiment, and at a mole ratio of about 40 to about 70 in another embodiment.

The techniques described above can be advantageously used for producing bis(hydroxyaryl)tricyclo[5.2.1.0$^{2,6}$]decane. The method generally comprises reacting a substituted or an unsubstituted tricyclo[5.2.1.0$^{2,6}$]decanone with an aromatic hydroxy compound in the presence of the sulfonic acid type ion exchange resin catalyst and the promoter. The promoter is selected from the group consisting of a mercaptan compound, a resorcinol compound, and mixtures thereof as previously described. For example, 5,5-bis(4-hydroxyphenyl)tricyclo[5.2.1.0$^{2,6}$]decane is produced by reacting phenol with TCD. TCD is available commercially from Celanese Chemicals.

For the purposes of this disclosure, catalytic activity at a given run time can be defined as the percentage of catalytic activity retained by a catalyst, relative to an initial catalytic activity. This catalyst activity, designated as S can be mathematically expressed as a percentage value using equation (1):

$$S=100*(w/w_0) \qquad (1);$$

where "w" represents the weight percent of p,p-DMBPC formed after a run time of "T" hours, and "w$_0$" represents the weight percent of p,p-DMBPC formed after about 16 hours of run time. This approach can be used for assessing the catalytic activity of sulfonic acid type ion exchange resin catalysts crosslinked with greater than or equal to 8 weight percent in a continuous process for producing p,p-DMBPC,
as described further below. Further, for the purposes of this disclosure, the amount of promoter used in the process is assumed to be constant.

Cycloalkylidene bisphenols prepared using the methods described above are valuable raw materials for preparing a variety of polycarbonate homopolymers and copolymers comprising structural units of formula (IV):

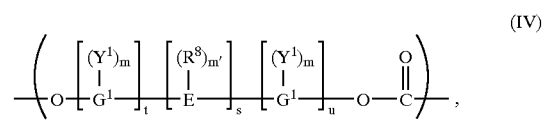

where G$^1$ is independently an aromatic group; E is an alkylene, an alkylidene, a cycloaliphatic group; a sulfur-containing linkage, a phosphorus-containing linkage; an ether linkage, a carbonyl group, or a tertiary nitrogen group, R$^8$ is independently a hydrogen or a monovalent hydrocarbon group; Y$^1$ is independently selected from the group consisting of a monovalent hydrocarbon group, alkenyl, allyl, halogen, bromine, chlorine; nitro; "m" represents any integer from and including zero through the number of positions on G$^1$ available for substitution; m' represents an integer from and including zero through the number of positions on E available for substitution; "t" represents an integer equal to at least one; "s" is either zero or one; and "u" represents any integer including zero.

In formula (IV), G$^1$ represents an aromatic group, such as phenylene, biphenylene, naphthylene, and the like aromatic groups. E may be an alkylene or alkylidene group such as methylene, ethylene, ethylidene, propylene, propylidene, isopropylidene, butylene, butylidene, isobutylidene, amylene, amylidene, isoamylidene, and the like. Alternatively, E may consist of two or more alkylene or alkylidene groups connected by a moiety different from alkylene or alkylidene, such as an aromatic linkage, a tertiary amino linkage, an ether linkage, a carbonyl linkage, a sulfur-containing linkage such as sulfide, sulfoxide, sulfone, a phosphorus-containing linkage such as phosphinyl, phosphonyl, and like linkages. In addition, E may comprise a cycloaliphatic group. R$^8$ independently represents a monovalent hydrocarbon group such as alkyl, aryl, aralkyl, alkaryl, cycloalkyl, and the like. Y$^1$ comprises a halogen (e.g., fluorine, bromine, chlorine, iodine, and the like); a nitro group; an alkenyl group, allyl group, the same as R$^8$ as previously described, an oxy group such as OR, and the like. In a preferred embodiment, Y$^1$ is inert to and unaffected by the reactants and reaction conditions used to prepare the polymer. The letter "m" represents any integer from and including zero through the number of positions on G$^1$ available for substitution; "p" represents an integer from and including zero through the number of positions on E available for substitution; "t" represents an integer equal to at least one; "s" is either zero or one; and "u" represents any integer including zero.

Dihydroxy aromatic compounds that can be used in conjunction with the cycloalkylidene bisphenols of formula (I) are generally of the formula (V):

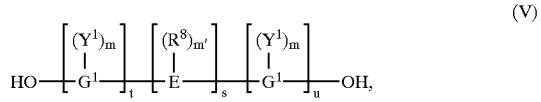

(V)

where $G^1$, E, $R^8$, "m", "t", and "u" are as previously described.

Specific examples of suitable bisphenols that can be used to form polycarbonate copolymers with the cycloalkylidene bisphenols of formula (I) can be selected from the group consisting of 4,4'-(3,3,5-trimethylcyclohexylidene)diphenol, 4,4'-bis(3,5-dimethyl)diphenol, 4,4-bis(4-hydroxyphenyl)heptane, 2,4'-dihydroxydiphenylmethane, bis(2-hydroxyphenyl)methane, bis(4-hydroxyphenyl)methane, bis(4-hydroxy-5-nitrophenyl)methane, bis(4-hydroxy-2,6-dimethyl-3-methoxyphenyl)methane, 1,1-bis(4-hydroxyphenyl)ethane, 1,1-bis(4-hydroxy-2-chlorophenyl)ethane, 2,2-bis(4-hydroxyphenyl)propane, 2,2-bis(3-phenyl-4-hydroxyphenyl)propane, 2,2-bis(4-hydroxy-3-methylphenyl)propane, 2,2-bis(4-hydroxy-3-ethylphenyl)propane, 2,2-bis(4-hydroxy-3-isopropylphenyl)propane, 2,2-bis(4-hydroxy-3,5-dimethylphenyl)propane, 2,2-bis(3,5,3',5'-tetrachloro-4,4'-dihydroxyphenyl)propane, bis(4-hydroxyphenyl)cyclohexylmethane, 2,2-1-phenylpropane, 2,4'-dihydroxyphenyl sulfone, 2,6-dihydroxy naphthalene; hydroquinone; resorcinol, $C_{1-3}$ alkyl-substituted resorcinols, 3-(4-hydroxyphenyl) -1,1,3-trimethylindan-5-ol, 1-(4-hydroxyphenyl)-1,3,3-trimethylindan-5-ol, 2,2,2',2'-tetrahydro-3,3,3',3'tetramethyl-1, ]'-spirobi[1H-indene]-6,6'-diol, ]-methyl- -1,3-bis(4-hydroxyphenyl)-3-isopropylcyclohexane, 1-methyl-2-(4-hydroxyphenyl) -3-[1-hydroxyphenyl) isopropyl]cyclohexane, and combinations thereof; and combinations comprising at least one of the foregoing bisphenols.

These polycarbonates can be generally produced by reaction of one or more cycloalkylidene bisphenols, or a cycloalkylidene bisphenol with any aromatic dihydroxy compound, with a suitable carbonic acid derivative, such as phosgene or a diaryl carbonate. Polycarbonates can also be produced by a solution process which involves condensation of one or more cycloalkylidene bisphenols with bis(chloroformate) derivatives of one or more aromatic dihydroxy compounds. The interfacial polycondensation of phosgene with a cycloalkylidene bisphenol in the presence of a suitable base, such as a tertiary amine gives the polycarbonate. The melt polycondensation of a cycloalkylidene bisphenol with a diaryl carbonate, such as diphenyl carbonate or bis(methylsalicyl)carbonate also affords polycarbonates. The solution process of reacting the bis(chloroformate) of a cycloalkylidene bisphenol with a dihydroxy aromatic compound is generally carried out in a solvent such as a halogenated hydrocarbon.

The disclosure is further illustrated with the following non-limiting examples.

EXAMPLES

In the following examples, the weight percent of cycloalkanone was determined by treatment of the sample with hydroxylamine hydrochloride, followed by titration of the liberated HCl. To measure the acid milliequivalency (expressed in meq/g) value, the ion exchange resin catalyst was first dried to remove all water. A weighed amount of the resin was then treated with aqueous NaCl to liberate HCl, and the isolated HCl solution was titrated to determine moles of acid present and calculate milliequivalents of acid/gram catalyst (meq/g) value. In all of the tables that follow hereinunder, "NA" stands for "not available".

The following examples employ one of the ion exchange resins shown in Table 1.

TABLE 1

| Tradename | Degree of crosslinking | Acid value meq/gram | Manufacturer |
|---|---|---|---|
| T-66 | 8% | ~5 | Thermax |
| T-63 | 18% | ~5 | Thermax |
| A-15 | 20% | ~5 | Rohm & Haas |
| A-121 | 2% | ~5 | Rohm & Haas |

Examples 1–2, and Comparative Examples 1–2

These Examples describe the batch reactions of TCD with phenol in the presence of various sulfonic acid type ion exchange resin catalysts shown in Table 1.

In these examples, TCD ketone (2 grams, available from) was added to a mixture of phenol (71 grams), Amberlyst®-15 ion exchange resin (3.65 grams), and 3-mercaptopropionic acid (0.73 gram) that had been pre-heated to 100° C. The mixture was agitated at 100° C. for 12 hours. GC analysis indicated that the conversion relative to TCD was 99.5%, and the weight percent yield of TCDBP based on TCD charge was 95%. The reaction mixture was distilled under vacuum to distill out about half the quantity of phenol. The hot residual material (at about 50° C.) was filtered to furnish the crude product as a pale pink solid in a yield of about 90% of theory. Recrystallization of the crude product from isopropyl alcohol gave TCDBP in a purity of >99.5 percent.

The weight percent yield of TCDBP and TCD ketone conversion for all the experiments run to prepare TCDBP are shown in Table 2. Examples 1* and 2* indicate Comparative Examples.

TABLE 2

| Ex. | Promoter (PPM) | Catalyst (Weight %) | Temp (° C.) | Weight percent selectivity for TCDBP | Weight percent TCD ketone conversion |
|---|---|---|---|---|---|
| 1 | 3-MPA (10000) | A-15 (3.7) | 100 | 95 | 99.5 |
| 2 | 3-MPA (10000) | T-66 (3.7) | 100 | 66 | 70 |
| 1* | 3-MPA (10000) | A-121 (3.7) | 100 | 27 | 30 |
| 2* | Resorcinol (10000) | A-121 (3.7) | 100 | 7 | 10 |

The results show that a combination of Amberlyst® 15 and 3-MPA (3-mercaptopropionic acid) gave a higher weight percent yield of TCDBP and weight percent conversion of TCD as compared to the combination of Amberlyst® 121 with 3-MPA or resorcinol as a promoter. As shown in Table 1, Amberlyst® 15 had a crosslinking density of 20%, whereas Amberlyst® 121 had a crosslinking density of 2 weight percent.

Examples 3–16

These Examples are directed to batch reactions of cyclohexanone with ortho-cresol in the presence of Amberlyst® 15 (A-15) catalyst and 3-MPA or resorcinol. All of these reactions were carried out at a reaction temperature of about 65° C. GC was used to analyze the reaction mixtures with the weight percent of p,p-DMBPC obtained directly from the GC analysis. Results are shown in Table 3. The term A/B refers to the mole ratio of ortho-cresol to cyclohexanone.

TABLE 3

| Ex | Promoter (PPM) | Weight percent of A-15 Catalyst | A/B | Weight percent yield of p,p-DMBPC after 7 h | 24 h |
|---|---|---|---|---|---|
| 3 | 3-MPA (200) | 10 | 30 | 54 | 77 |
| 4 | 3-MPA (600) | 10 | 30 | 66 | 87 |
| 5 | 3-MPA (1000) | 10 | 30 | 68 | 92 |
| 6 | Resorcinol (200) | 10 | 30 | 50 | 80 |
| 7 | Resorcinol (600) | 10 | 30 | 60 | 84 |
| 8 | Resorcinol (1000) | 10 | 30 | 66 | 86 |
| 9 | Resorcinol (1500) | 5 | 25 | 66 | 86 |
| 10 | Resorcinol (2500) | 5 | 25 | 84 | 91 |
| 11 | Resorcinol (3500) | 5 | 25 | 83 | 93 |
| 12 | Resorcinol (4500) | 5 | 25 | 87 | 89 |
| 13 | Resorcinol (10000) | 10 | 10 | 71 | NA |
| 14 | Resorcinol (10000) | 10 | 15 | 95 | NA |
| 15 | Resorcinol (10000) | 10 | 20 | 96 | NA |
| 16 | Resorcinol (10000) | 10 | 25 | 97 | NA |

The results in Table 3 show that in a batch process run with 3-MPA or resorcinol as promoter, the weight percent yield of p,p-DMBPC increases with increasing amount of resorcinol promoter, as well as increasing mole ratio of ortho-cresol to cyclohexanone. Further, Example 14 shows that good selectivity for p,p-DMBPC is observed with higher levels of resorcinol, even at ortho-cresol to cyclohexanone mole ratio of about 15.

Example 17

This Example describes the preparation of DMBPC using 3.5 parts of resorcinol promoter per 100 parts of the combined weights of ortho-cresol and cyclohexanone and hydrogen chloride gas as the catalyst.

A 500 mL four-necked, round-bottomed flask fitted with gas inlet, dropping funnel with gas outlet, overhead stirrer and a thermometer vented to a stirred scrubber containing 10 weight percent sodium hydroxide solution. The system was flushed with nitrogen, pre-warmed to 45° C., and charged with ortho-cresol (270.3 grams, 2.5 moles) and resorcinol (11.1 grams, 3.5 weight percent with respect to the combined weights of ortho-cresol and cyclohexanone). Dry hydrogen chloride gas was then bubbled through the reaction system with stirring until the atmosphere in the reactor appeared cloudy. To the stirred mixture was added cyclohexanone (49.2 grams, 0.5 mole) drop-wise over a period of about 1 hour, during which the color of the reaction mixture changed from colorless to yellowish-orange to purple. An exotherm was observed which resulted in the internal solution temperature reaching about 80° C. Excess hydrogen chloride gas was removed by bubbling nitrogen through the reaction mixture with nitrogen while the internal temperature was maintained at about 60° C. After about 15 minutes, the headspace in the reactor became clear, signifying that excess hydrogen chloride had been removed. The reaction mixture was then cooled to room temperature and filtered through Buchner funnel. The resulting filter cake was washed with 300 milliliters of ethylene dichloride, and dried in a vacuum oven maintained at about 60° C. and a pressure of about 1 millimeter of mercury. The yield of para, para-DMBPC was 121 grams, about 82% of theory. The purity of the product, as determined by HPLC was about 99.5 percent.

Example 18

This Example describes the preparation of DMBPC using the same procedure as described in Example 17, but with 3,500 parts per million of resorcinol promoter relative to the combined weights of ortho-cresol and cyclohexanone. The yield of para, para-DMBPC was 44 grams, about 74 percent of the theoretical yield. The purity of the product, as determined by HPLC, was about 97 percent.

Examples 19–21 and Comparative Examples 3–5

These Examples illustrate the effect of resorcinol promoter in the organic sulfonic acid-catalyzed reaction of cyclohexanone with ortho-cresol to produce DMBPC. The organic sulfonic acids used were 1-naphthalenesulfonic acid (NSA), dodecylbenzenesulfonic acid (DDBSA), or para-toluenesulfonic acid (PTSA). Reactions were carried out using about 10,000 ppm of resorcinol and an ortho-cresol to cyclohexanone of 5:1, respectively. Results are shown in Table 4.

TABLE 4

| Ex | Catalyst (Weight %) | Resorcinol (ppm) | Temp (° C.) | Weight percent yield of cycloalkylidene bisphenol after 7 hours reaction time |
|---|---|---|---|---|
| 19 | DDBSA (10) | 10000 | 35 | 54 |
| 20 | NSA (10) | 10000 | 65 | 81 |
| 21 | PTSA (10) | 10000 | 65 | 76 |
| 3* | BSA (1) | 10000 | 65 | 29 |
| 4* | BSA (1) | None | 35 | 26 |
| 5* | NSA (1) | None | 65 | 25 |
| 6* | DDBSA (5.5) | None | 50 | 1 |
| 7* | PTSA (10) | None | 35 | 7 |

*Indicates Comparative Examples where no promoter was used.

The results shown in Table 4 show that weight percent yields of p,p-DMBPC increased with organic sulfonic acids such as DDBSA, NSA, and PTSA. BSA gave a relatively poorer yield of p,p-DMBPC under comparable reaction conditions, whether or not resorcinol promoter was used.

Example 22

This Example describes the preparation of p,p-DMBPC using dodecylbenzenesulfonic acid (DDBSA) as catalyst and resorcinol as a promoter.

In a four-necked 500 ml round-bottomed flask equipped with a mechanical stirrer, a gas inlet tube, a thermometer pocket and a reflux condenser, was charged ortho-cresol (250 grams, 2.3 moles). The reactor system was flushed with nitrogen gas, and cyclohexanone (45 grams, 0.45 mole), dodecylbenzenesulfonic acid (38 grams, 12.6 weight percent relative to the combined weights of cyclohexanone and ortho-cresol), followed by resorcinol (3 grams, 10000 parts per million with respect to the combined weights of cyclohexanone and ortho-cresol). The reactor contents were stirred at ambient temperature for about one hour during which a mild exotherm occurred raising the internal temperature by about 3–5° C. The reaction mixture was then heated with stirring so as to bring the internal temperature to about 55° C. After being heated for 8 hours, the reaction mass was poured into 150 milliliters of toluene and stirred at ambient temperature for about 2 houres. The solid product was filtered, dried, washed with 50 milliliters of toluene, and filtered. The filter cake was transferred to a beaker, slurried with 150 milliliters of toluene, filtered, and the filter cake was washed with 50 milliliters of toluene. The solid product was finally dried to yield p,p-DMBPC in a yield of 109 grams, or 70 percent of theory, at a purity greater than 99 percent.

Examples 23–24 and Comparative Example 8

These Examples show the results of continuous reaction of cyclohexanone with ortho-cresol to illustrate the lifetime of the Amberlyst® 15 catalyst. The following procedure used for Example 24 is illustrative of the method used for these Examples and Comparative Example.

Amberlyst® 15 catalyst (12 grams) was packed in a jacketed glass column. The catalyst packing was held in place by a combination of glass wool and sand. The jacket was maintained at the temperature indicated in Table 5 by using a recirculating stream of heated oil. A feed mixture comprising cyclohexanone and ortho-cresol was prepared according to the mole ratio shown in Table 5 and fed at the top of the column. Addition of the feed was controlled by a pump so as to maintain the required weight hourly space velocity indicated in Table 5. Reactor effluent samples were collected at suitable times (as indicated in Table 5). A/B represents the mole ratio of ortho-cresol to cyclohexanone. Unreacted cycloalkanone was measured by using the same titration technique that is used for measuring acetone. Weight of p,p-DMBPC formed was measured by HPLC technique.

The same procedure was used for Example 23 and Comparative Example 8, but the appropriate amounts of ortho-cresol and cyclohexanone were taken so as to arrive at an ortho-cresol to cyclohexanone mole ratio of 13, 20, or 30. Results are shown in Table 5.

The data in Example 23 in Table 5 shows that at a mole ratio of about 30, after running the process for about 600 hours, the catalyst retained greater than about 98 percent of the initial catalytic activity measured after 16 hours of run time. The mole ratio used in Example 24 (18.6) is lower than in Example 23, but after about 400 hours, the catalyst retained about 73 percent of the initial catalytic activity measured after about 16 hours. However, at a mole ratio of about 13, and after a run time of about 400 hours, the catalyst retained only about 58 percent of its initial activity measured after about 16 hours of run time.

Examples 25–58

These Examples describe the short column reactor method used to screen MPA and resorcinol promoter at various loadings and reaction parameters. The experimental procedure used here was essentially the same as described for Examples 23, 24, and Comparative Example 8, except that the samples taken for analyses were collected after 24 hours of run time. The percent p,p-DMBPC selectivity is reported on a weight basis. The results are shown in Table 6.

TABLE 5

| Example | Promoter (ppm level) | WHSV | Temp. (° C.) | A/B | Weight percent of p,p - DMBPC in effluent formed after total run time (hours) | | | | | | | Catalytic activity (S) (percent) |
|---|---|---|---|---|---|---|---|---|---|---|---|---|
| | | | | | 16 | 100 | 200 | 300 | 400 | 500 | 600 | |
| 23 | 3-MPA (1000) | 1 | 75 | 30 | 8.1 | 8.0 | 7.9 | 8.0 | 8.0 | 8.1 | 8.0 | >98 |
| 24 | 3-MPA (1000) | 1 | 75 | 20 | 10.6 | 9.9 | 8.4 | 8.1 | 7.7 | NA | NA | 73 |
| 8* | 3-MPA (1000) | 1 | 75 | 13 | 11.2 | 8.0 | 7.2 | 6.7 | 6.5 | NA | NA | 58 |

*Indicates Comparative Example.

TABLE 6

| Example | Promoter (ppm level) | WHSV | Temperature (° C.) | o-cresol to cyclohexanone mole ratio | Percent p,p-DMBPC selectivity | Percent Cyclohexanone Conversion |
|---|---|---|---|---|---|---|
| 25 | 3-MPA (3000) | 1.5 | 65 | 30 | 92.8 | 71.4 |
| 26 | 3-MPA (3000) | 1.5 | 75 | 30 | 89.8 | 84.9 |
| 27 | 3-MPA (3000) | 1 | 65 | 30 | 92.6 | 83 |
| 28 | 3-MPA (3000) | 1 | 75 | 30 | 89.3 | 87.3 |
| 39 | 3-MPA (3000) | 0.5 | 65 | 30 | 92.3 | 86.4 |
| 30 | 3-MPA (3000) | 0.5 | 75 | 30 | 88.7 | 86.3 |
| 31 | 3-MPA (3000) | 0.25 | 65 | 30 | 90.8 | NA |
| 32 | 3-MPA (3000) | 0.25 | 75 | 30 | 87.8 | NA |
| 33 | Resorcinol (3000) | 1.5 | 65 | 30 | 88.9 | 63.4 |
| 34 | Resorcinol (3000) | 1 | 65 | 30 | 91.7 | 77.3 |
| 35 | Resorcinol (3000) | 1 | 75 | 30 | 86.6 | 88.1 |
| 36 | Resorcinol (3000) | 0.5 | 65 | 30 | 88.8 | 81.7 |
| 37 | Resorcinol (3000) | 0.5 | 75 | 30 | 86.8 | 88.9 |
| 38 | Resorcinol (3000) | 0.25 | 65 | 30 | 90.3 | NA |
| 39 | Resorcinol (3000) | 0.25 | 75 | 30 | 87.9 | 92.7 |
| 40 | 3-MPA (3000) | 1 | 65 | 16 | 88.3 | 68.7 |
| 41 | 3-MPA (3000) | 1 | 75 | 16 | 85.6 | 84.2 |
| 42 | 3-MPA (3000) | 2 | 65 | 16 | 87.2 | 56.8 |
| 43 | 3-MPA (3000) | 2 | 75 | 16 | 81.4 | 55.9 |
| 44 | 3-MPA (3000) | 2 | 55 | 16 | 82.5 | 37.0 |

TABLE 6-continued

| Example | Promoter (ppm level) | WHSV | Temperature (° C.) | o-cresol to cyclohexanone mole ratio | Percent p,p-DMBPC selectivity | Percent Cyclohexanone Conversion |
|---|---|---|---|---|---|---|
| 45 | 3-MPA (3000) | 2 | 85 | 16 | 75.6 | 57.7 |
| 46 | 3-MPA (3000) | 1 | 65 | 6 | 85.7 | 49.6 |
| 47 | 3-MPA (3000) | 1 | 75 | 6 | 83.5 | 46.6 |
| 48 | 3-MPA (3000) | 2 | 65 | 6 | 82.9 | 30.5 |
| 49 | 3-MPA (3000) | 2 | 75 | 6 | 79.5 | 30.7 |
| 50 | 3-MPA (3000) | 0.5 | 75 | 6 | 79.9 | 41.5 |
| 51 | 3-MPA (3000) | 1 | 65 | 25 | 88.3 | 73.3 |
| 52 | 3-MPA (3000) | 1 | 75 | 25 | 84.1 | 79.8 |
| 53 | 3-MPA (3000) | 0.5 | 65 | 25 | 87.5 | 79.2 |
| 54 | 3-MPA (3000) | 0.5 | 75 | 25 | 80.4 | 84.6 |
| 55 | 3-MPA (15000) | 1 | 65 | 25 | 85.6 | 78.1 |
| 56 | 3-MPA (15000) | 1 | 75 | 25 | 78.4 | 75.8 |
| 57 | 3-MPA (15000) | 0.5 | 65 | 25 | 84.9 | 68.6 |
| 58 | 3-MPA (15000) | 0.5 | 75 | 25 | 77.2 | 71.4 |

The data shows that the resorcinol and 3-MPA promoters, in combination with Amberlyst® 15 ion exchange resin catalyst are effective for forming p,p-DMBPC in high selectivity.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A continuous process for forming a cycloalkylidene bisphenol, comprising:
reacting an aromatic hydroxy compound and a cycloalkanone compound in the presence of a sulfonic acid type ion exchange resin catalyst and a promoter; wherein said cycloalkanone compound is selected from the group consisting of substituted and unsubstituted tricyclo[5.2.1.0$^{2,6}$]decanones, and 4-perhydrocumyl cyclohexanone, wherein a mole ratio of said aromatic hydroxy compound to said cycloalkanone is greater than or equal to about 20; wherein said sulfonic acid type ion exchange resin catalyst is crosslinked with greater than or equal to about 8 weight percent of divinylbenzene relative to an overall weight of said sulfonic acid type ion exchange resin catalyst, and has a catalytic activity after at least 100 hours of run time that is greater than or equal to about 70 percent of an initial catalytic activity that was measured after about 16 hours of run time; and wherein said promoter is selected from the group consisting of a mercaptan compound and a resorcinol compound; and
forming the cycloalkylidene bisphenol having the formula:

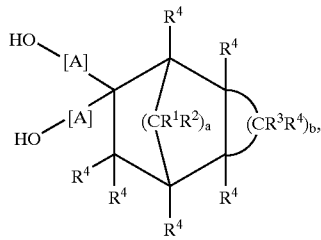

wherein [A] is a substituted or an unsubstituted aromatic group, $R^1$–$R^4$ independently represent a hydrogen or a $C_1$–$C_{12}$ hydrocarbyl group; and "a" and "b" are integers independently having values from 0 to 3.

2. The process of claim 1, wherein said sulfonic acid type ion exchange resin catalyst is crosslinked with about 20 weight percent of divinylbenzene relative to the overall weight of said sulfonic acid type ion exchange resin catalyst.

3. The process of claim 1, wherein said mercaptan compound is selected from the group consisting of 3-mercaptopropionic acid, a substituted or an unsubstituted benzyl mercaptan, 3-mercapto-1-propanol, ethyl 3-mercaptopropionate, 1,4-bis(mercaptomethyl)benzene, alkanethiols of the formula R-SH, wherein "R" is a $C_1$ to $C_{10}$ hydrocarbyl group; and mixtures of the foregoing mercaptan compounds.

4. The process of claim 1, wherein said resorcinol compound is of the formula:

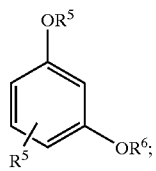

wherein $R^5$ is selected from the group consisting of hydrogen, chlorine, fluorine, bromine, and $C_1$–$C_{10}$ alkyl groups; and $R^6$ is selected from the group consisting of $C_1$–$C_{10}$ alkyl groups.

5. The process of claim 1, wherein said resorcinol compound is selected from the group consisting of resorcinol, 2-methylresorcinol, resorcinol diethyl ether, resorcinol dimethylether, 4-hexylresorcinol, 4-chlororesorcinol, and any combinations of the foregoing resorcinol compounds.

6. The process of claim 1, wherein reacting the aromatic hydroxy compound and the cycloalkanone compound in the presence of the sulfonic acid type ion exchange resin catalyst and the promoter comprises passing the aromatic hydroxy compound and the cycloalkanone compound through the packed bed comprising said sulfonic acid type ion exchange resin catalyst at a weight hourly space velocity from about 0.25 to about 4.

7. The process of claim 1, wherein said aromatic hydroxy compound is selected from the group consisting of phenol; ortho-cresol, meta-cresol, para-cresol, 2,6-xylenol, and mixtures of the foregoing aromatic hydroxy compounds.

8. The process of claim 1, wherein said reacting the aromatic hydroxy compound and the cycloalkanone compound in the presence of the sulfonic acid type ion exchange resin catalyst and the promoter is in a batch, a semi-batch, or a continuous mode.

9. A method of making a polycarbonate which comprises reacting a carbonic acid derivative with a cycloalkylidene bisphenol, said cycloalkylidene bisphenol being prepared by a continuous method comprising:
reacting an aromatic hydroxy compound and a cycloalkanone compound in the presence of a sulfonic acid type ion exchange resin catalyst and a promoter, wherein said cycloalkanone compound is selected from the group consisting of substituted and unsubstituted tricyclo[5.2.1.0$^{2,6}$]decanones, and 4-perhydrocumyl cyclohexanone wherein a mole ratio of said aromatic hydroxy compound to said cycloalkanone is greater than or equal to about 20, wherein said sulfonic acid type ion exchange resin catalyst is crosslinked with greater than or equal to about 8 weight percent of divinylbenzene relative to an overall weight of said sulfonic acid type ion exchange resin catalyst and has a catalytic activity that is greater than or equal to about 70 percent of an initial catalytic activity which was measured after about 16 hours of run time, and wherein said promoter is selected from the group consisting of a mercaptan compound and a resorcinol compound; and
forming the cycloalkylidene bisphenol having the formula:

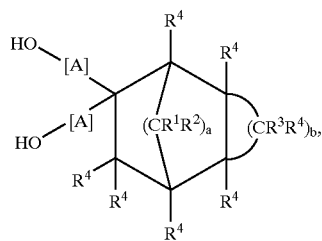

wherein [A] is a substituted or an unsubstituted aromatic group, R$^1$–R$^4$ independently represent a hydrogen or a C$_1$–C$_{12}$ hydrocarbyl group; and "a" and "b" are integers independently having values from 0 to 3.

10. A method for preparing a cycloalkylidene bisphenol, comprising:
reacting a mixture comprising an aromatic hydroxy compound and a cycloalkanone compound in the presence of an acid catalyst and a resorcinol compound, wherein said cycloalkanone compound is selected from the group consisting of substituted and unsubstituted tricyclo[5.2.1.0$^{2,6}$]decanones, and 4-perhydrocumyl cyclohexanone wherein a mole ratio of said aromatic hydroxy compound to said cycloalkanone is greater than or equal to about 20, said acid catalyst being selected from the group consisting of a sulfonic acid type ion exchange resin catalyst which is crosslinked with greater than or equal to about 8 weight percent of divinylbenzene relative to an overall weight of said sulfonic acid type ion exchange resin catalyst; and an organic sulfonic acid; and
forming said cycloalkylidene bisphenol of the formula:

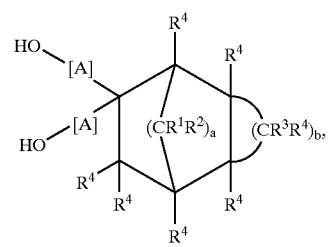

wherein [A] is a substituted or an unsubstituted aromatic group, R$_1$–R$^4$ independently represent a hydrogen or a C$_1$–C$_{12}$ hydrocarbyl group; and "a" and "b" are integers independently having values from 0 to 3.

11. The method of claim 10, wherein said cycloalkanone is selected from the group consisting of substituted and unsubstituted tricyclo decanones, and substituted and unsubstituted cyclohexanones.

12. The method of claim 10, wherein said organic sulfonic acid is selected from the group consisting of para-toluenesulfonic acid, naphthalenesulfonic acid, methamesulfonic acid, and dodecylbenzenesulfonic acid.

13. The method of claim 10, wherein said resorcinol compound is selected from the group consisting of resorcinol, 2-methylresorcinol, resorcinol diethyl ether, resorcinol dimethylether, 4-hexylresorcinol, 4-chlororesorcinol, and any combinations of the foregoing resorcinol compounds.

14. The method of claim 10, further comprising adding a mercaptan compound to the mixture.

15. The method of claim 14, wherein said mercaptan compound is selected from the group consisting of 3-mercaptopropionic acid, a substituted or an unsubstituted benzyl mercaptan, 3-mercapto-1-propanol, ethyl 3-mercaptopropionate, 1,4-bis(mercaptomethyl)benzene, alkanethiols of the formula R-SH, wherein "SR" is a C$_1$ to C$_{10}$ hydrocarbyl group, and mixtures of the foregoing mercaptan compounds.

16. The method of claim 10, wherein said aromatic hydroxy compound is selected from the group consisting of phenol, ortho resol, meta-cresol, para-cresol, 2,6-xylenol, and mixtures of the foregoing aromatic hydroxy compounds.

17. The method of claim 10, wherein said reacting the aromatic hydroxy compound and the cycloalkanone compound in the presence of the sulfonic acid type ion exchange resin catalyst and the promoter is in a batch or a continuous mode.

18. A method for producing 1,1-bis(3-methyl-4-hydroxyphenyl)cyclohexane, said method comprising:
reacting a mixture comprising ortho-cresol and cyclohexanone in the presence of from 10 to 15 weight percent of dodecylbenzenesulfonic acid, relative to a combined weight of ortho-cresol and cyclohexanone; and from 5000 to 15000 parts of resorcinol per million parts of the combined weights of cyclohexanone and ortho-cresol to form 1,1-bis(3-methyl-4-hydroxyphenyl)cyclohexane.

19. The method of claim 18, wherein said reacting further comprises maintaining a reaction temperature from about 50° C. to about 60° C.

20. The method of claim 18, wherein said reacting comprises a ortho-cresol to cyclohexanone mole ratio of from about 10 to about 40.

21. The method of claim 18, wherein said reacting comprises a reaction time of about 7 hours to about 36 hours.

* * * * *